United States Patent
Pernu et al.

(10) Patent No.: US 10,772,518 B2
(45) Date of Patent: Sep. 15, 2020

(54) SYSTEM AND METHOD FOR HEART RATE MONITORING OF AN OBJECT

(71) Applicant: Suunto Oy, Vantaa (FI)

(72) Inventors: Kimmo Pernu, Vantaa (FI); Mikko Martikka, Vantaa (FI); Erik Lindman, Vantaa (FI)

(73) Assignee: Suunto Oy, Vantaa (FI)

( * ) Notice: Subject to any disclaimer, the term of this patent is extended or adjusted under 35 U.S.C. 154(b) by 124 days.

(21) Appl. No.: 15/836,969

(22) Filed: Dec. 11, 2017

(65) Prior Publication Data
US 2018/0168462 A1 Jun. 21, 2018

(30) Foreign Application Priority Data

Dec. 21, 2016 (FI) ..................................... 20166001
Dec. 21, 2016 (GB) .................................. 1621793.7

(51) Int. Cl.
| | | |
|---|---|---|
| A61B 5/0245 | (2006.01) |
| A61B 5/00 | (2006.01) |
| A61B 5/11 | (2006.01) |
| A61B 5/024 | (2006.01) |
| A61B 5/0456 | (2006.01) |
| G16H 40/67 | (2018.01) |
| G06K 9/00 | (2006.01) |

(Continued)

(52) U.S. Cl.
CPC .......... *A61B 5/0245* (2013.01); *A61B 5/0006* (2013.01); *A61B 5/0022* (2013.01); *A61B 5/02438* (2013.01); *A61B 5/0456* (2013.01); *A61B 5/1118* (2013.01); *A61B 5/681* (2013.01); *G01C 22/006* (2013.01); *G01P 15/0802* (2013.01); *G06K 9/00342* (2013.01); *G16H 40/67* (2018.01); *A61B 5/7275* (2013.01); *A61B 2503/10* (2013.01)

(58) Field of Classification Search
CPC . A61B 5/0245; A61B 5/0456; A61B 5/02438; A61B 5/0006; A61B 5/681; A61B 5/1118; A61B 5/0022; A61B 2503/10; A61B 5/7275; G16H 40/67; G06K 9/00342; G01P 15/0802; G01C 22/006
See application file for complete search history.

(56) References Cited

U.S. PATENT DOCUMENTS

| | | |
|---|---|---|
| D676,137 S | 2/2013 | Lindberg et al. |
| 8,974,396 B1 | 3/2015 | Brady et al. |
| D739,943 S | 9/2015 | Pernu et al. |

(Continued)

FOREIGN PATENT DOCUMENTS

| | | | |
|---|---|---|---|
| EP | 2294978 | * | 3/2011 |
| EP | 2294978 A1 | | 3/2011 |

(Continued)

*Primary Examiner* — Catherine M Voorhees
(74) *Attorney, Agent, or Firm* — Laine IP Oy

(57) ABSTRACT

According to an example aspect of the present invention, there is provided a system for heart rate monitoring of an object, the system comprising means for measuring heart beats of the object with a first unit at a first sampling rate, determining a heart rate, determining a time difference between consecutive heart beats, determining a time of each heart beat, or determining at least a part of a wave form of a heart beat signal, wherein the first unit includes further means for changing the sampling rate as a response to the determined information.

23 Claims, 4 Drawing Sheets

(51) Int. Cl.
*G01C 22/00* (2006.01)
*G01P 15/08* (2006.01)

(56) References Cited

U.S. PATENT DOCUMENTS

| | | | |
|---|---|---|---|
| D739,944 S | 9/2015 | Pernu et al. | |
| 9,144,385 B1 | 9/2015 | Brady et al. | |
| 9,167,975 B1 | 10/2015 | Brady et al. | |
| 9,179,849 B1 | 11/2015 | Brady et al. | |
| 9,314,174 B1 | 4/2016 | Brady et al. | |
| 2014/0073982 A1* | 3/2014 | Yang | A61B 5/0456 600/521 |
| 2014/0135612 A1 | 5/2014 | Yuen et al. | |
| 2014/0273858 A1* | 9/2014 | Panther | A61B 5/0002 455/41.2 |
| 2015/0057111 A1* | 2/2015 | Tremblay-Munger | A63B 69/0026 473/446 |
| 2015/0257669 A1 | 9/2015 | Ben-David et al. | |
| 2015/0265170 A1 | 9/2015 | Wisloff et al. | |
| 2016/0029898 A1* | 2/2016 | LeBoeuf | A61B 5/0205 600/301 |

FOREIGN PATENT DOCUMENTS

| | | |
|---|---|---|
| EP | 2921105 A1 | 9/2015 |
| WO | WO2007092543 A2 | 8/2007 |
| WO | WO 2013019494 A2 | 2/2013 |
| WO | WO2014060938 A1 | 4/2014 |
| WO | WO 2014177763 A1 | 11/2014 |
| WO | WO2014197822 A2 | 12/2014 |
| WO | WO2016029166 A1 | 2/2016 |

\* cited by examiner

SYSTEM AND METHOD FOR HEART RATE MONITORING OF AN OBJECT

FIELD

The present invention relates to a system for heart rate monitoring of an object. Further, the present invention relates to a method for heart rate monitoring of an object. Furthermore, the present invention relates to a computer readable memory. Additionally, the present invention relates to a computer program.

BACKGROUND

There are a number of different devices and methods for measuring, calculating or estimating the heart rate of a person. Heart rate monitors and similar wristop computers may, for example, include a transmitter belt attached to the human body by a flexible belt, which nowadays typically measures the pulse. The term heart rate monitor refers to a wristop computer or some other corresponding device, equipped with heart rate monitor properties. Such heart rate measurement may e.g. take place during motion of the person. The measuring device equipped with electrodes transmits measurement data wirelessly to e.g. a wristwatch-like wristop computer, in which at least a part of the received signal is processed and displayed on the display of the wristop computer. The pulse data of the person may be also stored on said wristop computer. Known wristop computers can be used to measure not only pulse, but also, for example, blood pressure, speed, acceleration, distance traveled, and direction data.

With regards to pulse measurement, one or more sensors may be positioned against the chest, neck, wrist, auricle or foot of a person. Portable devices that measure the heart beats may make use of a chest belt or a wrist watch, for instance. The devices measure the electric signal of the heart (ECG), for example during the person's physical activity. The electrical activity of the heart is measured over a period of time using electrodes placed on the skin of the person. Documents U.S. D739,944 S, U.S. D739,943 S, and U.S. D676,137 S for example illustrate different heart rate belts.

The measurement information is typically transmitted from the heart rate belt to the wristop computer wirelessly. If several persons using wristop computers are close to each other, the receiver must identify the correct transmitter. In newer devices, digital signal transfer with digital identification codes has been used, for instance. In this solution, the transmitter belt includes a set of circuits, which are used to detect the heartbeats and create pulse-interval information, which states the length of time between the detected heartbeats. The pulse-interval data is coded into a digital signal, which is transmitted to the wristop computer. Subsequently, the pulse-interval data may be analysed by the wristop computer prior to displaying the pulse data on the display of the wristop computer. Additionally or instead, the pulse data of the person may be stored on said wristop computer.

Certain devices for heart rate monitoring measure a sufficient amount of data to form a wave form of a pulse and other devices only measure the time interval between two consecutive heartbeats, i.e. the pulse-interval data. Systems providing a wave form of a pulse have to process and/or store more data than systems providing only pulse-interval data. However, systems providing a wave form of a pulse may be of more use e.g. for a doctor or other medical personal for a diagnosis after reading out the memory.

Of course, energy consumption takes place by means of such measurement, analysis, and storing of pulse data. Consequently, portable measurement devices are equipped with at least one power source such as a battery. Systems providing a wave form of a pulse consume more energy than systems providing only pulse-interval data, since continuous measurement of the electric signal of the heart is required for measuring a wave form of a pulse. Further, for both different systems a sufficient memory has to be provided in order to store the pulse data by means of the wristop computer.

In view of the foregoing, it would be beneficial to provide a system for heart rate monitoring of an object, which system is able to reduce energy consumption during measurement of the heart beats and/or is able to reduce required memory.

An example of a heart rate monitor is disclosed in Document U.S. Pat. No. 9,167,975 B1. The document discloses a motion resistant device to monitor heart rate in ambulatory patients. The device allows for a continuous heart rate to be collected and recorded for extended time frames equivalent to a Holter monitor or special pulse oximeter.

Documents U.S. Pat. No. 9,179,849 B1 and U.S. Pat. No. 9,314,174 B1 describe a mobile plethysmographic device for detecting a premature ventricular contraction event. The mobile plethysmographic device generates a pleth waveform, which is automatically screened by algorithms that measure the waveform to correlate, detect and store aberrations related to heart anomalies. A premature ventricular contraction event for a patient is determined based on an identification of a time interval of the pleth waveform that is below the threshold minimum time interval followed immediately by a time interval that is above the threshold maximum tine interval.

Documents U.S. Pat. No. 9,144,385 B1 and U.S. Pat. No. 8,974,396 B1 teach a mobile plethysmographic device for detecting a premature atrial contraction event. The mobile plethysmographic device generates a pleth waveform, which is automatically screened by algorithms that measure the waveform to correlate, detect and store aberrations related to heart anomalies. A premature atrial contraction event for a patient is determined based on an identification of a time interval of the pleth waveform that is below the threshold minimum time interval followed immediately by a time interval that is above the threshold maximum tine interval.

SUMMARY OF THE INVENTION

The invention is defined by the features of the independent claims. Some specific embodiments are defined in the dependent claims.

According to a first aspect of the present invention, there is provided a system for heart rate monitoring of an object, the system comprising means for measuring heartbeats of the object with a first unit at a first sampling rate, determining a heart rate, a time difference between consecutive heart beats, a time of each heart beat, or at least a part of a wave form of a heart beat signal, wherein the first unit includes further means for changing the sampling rate as a response to the determined information.

Various embodiments of the first aspect may comprise at least one feature from the following bulleted list:

- the determined heart rate information, the determined time difference information, the determined time of each heart beat, or the at least partially determined wave form of a heart beat signal is wirelessly transmitted to a second unit for further analyzing the decision on changing the sampling rate is made by the first unit or the second unit the system includes means for increasing the sampling rate if there is a decrease more than 25% in the measured R-R interval the system includes means for storing at least one of the measured heart beat information, the heart rate information, the time difference information, the information of the time of each heart beat, and at least the part of the wave form of the heart beat signal into the first unit the system includes means for transmitting and storing at least one of the measured heart beat information, the heart rate information, the time difference information, the information of the time of each heart beat, and at least the part of the wave form of the heart beat signal into the second unit the system includes means for increasing the sampling rate such that at least a partial wave form of one pulse can be formed the system includes means for decreasing the sampling rate if the R-R interval increases more than 33% and increasing the sampling rate if the R-R interval decreases more than 25% the system includes means for storing the data measured with the increased heart rate the system is portable the system is configured to change the sampling rate based on a beat-to-beat variability in R-R interval the system comprises a memory configured to store first-type sensor data, at least one processing core configured to compile a message based at least partly on the first-type sensor data, to cause the message to be transmitted from the system, to cause receiving in the system a machine readable instruction, using the machine readable instruction, based at least partly on sensor data. According to a second aspect of the present invention, there is provided a method for monitoring a heart rate of an object, the method comprising measuring heart beats of an object with a first unit at a first sampling rate, determining a heart rate, a time difference between consecutive heart beats, a time of each heart beat, or at least a part of a wave form of a heart beat signal, and changing the sampling rate as a response to the determined information.

Various embodiments of the second aspect may comprise at least one feature from the following bulleted list:

the determined heart rate information, the determined time difference information, the determined time of each heart beat, or the at least partially determined wave form of a heart beat signal is wirelessly transmitted to a second unit for further analyzing the decision on changing the sampling rate is made by the first unit or the second unit changing of the sampling rate takes place by means of further means of the first unit the sampling rate is increased if there is a decrease of more than 25% in the measured R-R interval at least one of the measured heart beat information, the heart rate information, the time difference information, the information of the time of each heart beat, and at least the part of the wave form of the heart beat signal is stored into the first unit at least one of the measured heart beat information, the heart rate information, the time difference information, the information of the time of each heart beat, and at least the part of the wave form of the heart beat signal is transmitted and stored into the second unit the sampling rate is increased such that at least a partial wave form of one pulse can be formed the sampling rate is decreased if the R-R interval increases more than 33% and is increased if the R-R interval decreases more than 25% the data measured with the increased sampling rate is stored the sampling rate is changed based on a beat-to-beat variability in R-R interval the method further comprises storing first-type sensor data in a system, compiling a message based at least partly on the first-type sensor data, causing the message to be transmitted from the system, causing receiving, responsive to the message, in the system a machine readable instruction, using the machine readable instruction, based at least partly on sensor data optionally, the estimated activity type or the nature of the activity may be derived from the first-type sensor data at least a part of a wave form of a heart beat signal is determined at the first sampling rate in first time intervals and subsequently at least a part of a wave form of a heart beat signal is determined at the second sampling rate continuously or in second time intervals shorter than the first time intervals According to a third aspect of the present invention, there is provided a computer readable memory having stored thereon a set of computer implementable instructions capable of causing a computing device, in connection with a system for heart rate monitoring of an object to measure heart beats of an object with a first unit at a first sampling rate, determine a heart rate, a time difference between consecutive heart beats, a time of each heart beat, or least a part of a wave form of a heart beat signal, and change the sampling rate as a response to the determined information.

Various embodiments of the third aspect may comprise at least one feature corresponding to a feature from the preceding bulleted list laid out in connection with the second aspect.

According to a fourth aspect of the present invention, there is provided a non-transitory computer readable medium having stored thereon a set of computer readable instructions that, when executed by at least one processor, cause an apparatus to at least measure heart beats of an object with a first unit at a first sampling rate, determine a heart rate, a time difference between consecutive heart beats, a time of each heart beat, or at least a part of a wave form of a heart beat signal, and change the sampling rate as a response to the determined information.

Various embodiments of the fourth aspect may comprise at least one feature corresponding to a feature from the preceding bulleted list laid out in connection with the second aspect.

According to a fifth aspect of the present invention, there is provided a computer program configured to cause a method in accordance with at least one of the method claims to be performed.

Considerable advantages are obtained by means of certain embodiments of the present invention. A system for heart rate monitoring of an object is provided. The system may be a portable device, for instance. The system for heart rate monitoring of the object is able to reduce energy consumption during measurement of heart beats.

In a first operational mode, the heart beats of the object are measured in a first unit by a first sampling rate. Subsequently, the heart rate information, time difference information between consecutive heart beats, the information of the time of each heart beat, or at least a part of a wave form of a heart beat signal is determined. The determined information may be e.g. transmitted wirelessly to a second unit for further analyzing. In a second operational mode, the sampling rate is changed as a response to the determined information. In other words, certain embodiments of the invention provide a system which allows to switch from a first operational mode into a second operational mode.

Typically, the time interval between consecutive heart beats, i.e. the pulse-interval, does not vary or does only vary very limited within a certain tolerance range. Such consecutive heart beats are measured in the first operational mode. In case that the time interval between consecutive heart beats varies unexpectedly, the system switches into the second operational mode and measures the heart beats at another sampling rate. In the second operational mode typically more heart beat information is measured than in the first operational mode. Other situations which may cause switching from the first operational mode into the second operational mode are exceeding a specific heart rate or falling below a specific heart rate, for instance.

According to certain embodiments of the present invention, it is not required to continuously measure full wave forms of pulses. At least a part of a wave form or full wave forms of a pulse is/are only measured in case of unexpected changes in the pulse-interval, which changes may be e.g. an indication of a physical problem of the heart and appear to be or are considered as "un-normal".

Consequently, in the first operational mode typically less energy is consumed than in the second operational mode, because of the different sampling rates. Additionally, in the first operational mode typically less memory is required for storing pulse data than in the second operational mode. Thus, certain embodiments of the present invention do not only reduce energy consumption, but also store less pulse data, while simultaneously providing the possibility to monitor unexpected ("un-normal") changes of the heart rate and measuring at least a part of a wave form or full wave forms.

The system for heart rate monitoring of an object according to certain embodiments of the invention can be manufactured in industrial scale.

EMBODIMENTS

Figure 1:
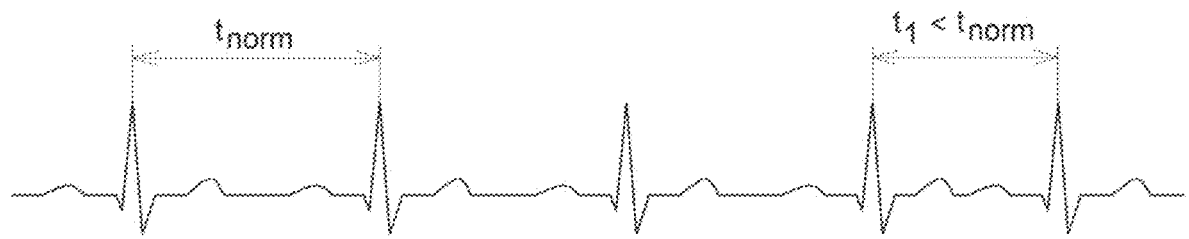
FIG. 1 illustrates a schematic view of consecutive heart beats.

In FIG. 1 a schematic view of consecutive heart beats is illustrated. The system in accordance with certain embodiments of the present invention is configured to measure heart beats and to determine the time interval between consecutive heart beats, i.e. the heart rate. Typically, the time interval, i.e. the pulse-interval, between consecutive heart beats does not vary or does only vary very limited within a certain tolerance range. In this document the time interval between such consecutive heart beats is defined as first pulse interval or "normal" pulse interval $t_{norm}$.

However, the time interval between consecutive heart beats may e.g. vary unexpectedly below or above a certain minimum or maximum tolerance value, respectively. In this document such a time interval between such consecutive heart beats is defined as second pulse interval $t_1$. Such a second pulse interval $t_1$ may be considered as "un-normal". Said second pulse interval $t_1$ may be, for example, shorter than the first time interval $t_{norm}$. Such a change in the heart rate may be e.g. an indication of a physical problem of the heart. Of course, second pulse interval $t_1$ may be, for example, also longer than the first time interval $t_{norm}$. Also such a change of the second pulse interval $t_1$ may be considered as "un-normal". The system according to certain embodiments of the invention allows to detect such changes in the heart rate.

In accordance with at least some embodiments of the present invention, there is provided a system for heart rate monitoring of an object comprising means for measuring heart beats of the object with a first unit at a first sampling rate, determining a heart rate, determining a time difference between consecutive heart beats, determining a time of each heart beat, or determining at least a part of a wave form of a heart beat signal, wherein the first unit includes further means for changing the sampling rate as a response to the determined information.

In other words, the system in accordance with at least some embodiments of the present invention is configured to measure the heart beats of the object at a first sampling rate. In case of an unexpected change in the heart rate, the system is configured to change the sampling rate in order to provide at least a part of a wave form of a pulse. The system allows to switch from a first operational mode into a second operational mode.

Normally, the sinus rhythm of a healthy heart is in the range between 60 heart beats/minute and 100 heart beats/minute.

A sinus rhythm of less than 60 heart beats/minute is called sinus bradycardia. A sinus rhythm of higher than 100 heart beats/minute is called sinus tachycardia. The sinus interval may be also irregular such that the longest PP- or RR-interval exceeds the shortest interval by 0.16 s. Such a situation is called sinus arrhythmia. Other situations known to the skilled person are called non-sinus atrial rhythm, wandering pacemaker, paroxysmal atrial tachycardia, atrial flutter, atrial fibrillation, junctional rhythm, ventricular arrhythmias, premature ventricular contraction, idioventricular rhythm, ventricular tachycardia, ventricular fibrillation, and pacer rhythm, for instance. Some specific embodiments of the system according to the present invention are capable of changing the sampling rate as a response to determined information due to at least one of the aforementioned situations.

Figure 2:
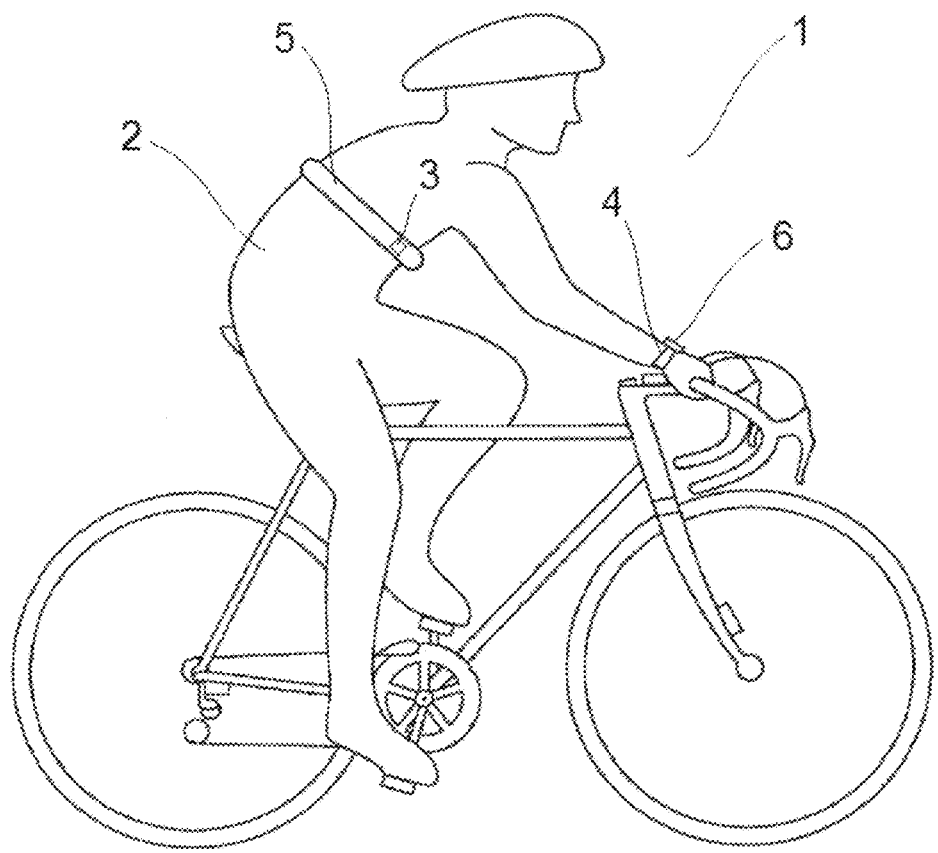
FIG. 2 illustrates a schematic view of a portable system for heart rate monitoring of an object in accordance with at least some embodiments of the present invention.

In FIG. 2 a schematic view of a portable system 1 for heart rate monitoring of an object 2 in accordance with at least some embodiments of the present invention is illustrated. The system 1 for heart rate monitoring of the object 2 comprises means for measuring the heart beats of an object 2 in a first unit 3 at a first sampling rate. Said means are arranged in connection with e.g. a heart rate belt 5. The first pulse interval $t_{norm}$ is measured at the first sampling rate.

The system 1 for heart rate monitoring of the object 2 further comprises means for determining a heart rate and transmitting the heart rate information wirelessly to a second unit 4 for further analyzing, or determining a time difference between consecutive heart beats and transmitting the time difference information wirelessly to the second unit 4 for further analyzing, or determining a time of each heart beat (time stamp) and transmitting the information of the time (time stamp) of each heart beat wirelessly to the second unit 4 for further analyzing. The second unit 4 e.g. comprises a wristop computer 6 or any other computing device. The wristop computer 6 is configured to analyze if the time intervals between consecutive heart beats have varied below or above a certain minimum or maximum tolerance value. The second unit may inter alia e.g. calculate the difference in consecutive pulse intervals. If the time intervals between consecutive heart beats have varied below or above a certain minimum or maximum tolerance value, a signal is transmitted to the first unit 3 in order to change the sampling rate.

The first unit 3 includes further means for changing the sampling rate as a response to the transmitted information. According to certain embodiments, the system may include means for increasing the sampling rate if there is a decrease of more than 25% in the measured R-R interval. Further, the system may include means for storing at least one of the measured heart beat information, the heart rate information, the time difference information, and the information of the time of each heart beat into the first unit 3. Furthermore, the system may include means for transmitting and storing at least one of the measured heart beat information, the heart rate information, the time difference information, and the information of the time of each heart beat into the second unit 4. Additionally, the system includes means for increasing the sampling rate such that at least a partial wave form of one pulse can be formed.

The duration of a QRS-complex is typically 0.06-0.10 seconds. This requires at least 32 Hz to capture something of that complex. A minimum R-R interval is typically 250 ms. $250 \text{ ms}*1.333^7$ is about 1873 ms. Thus, eight frequency categories can be used for the human R-R interval range of 250-2000 ms. According to certain embodiments, the maximum sampling rate is 256 Hz. Each step is 32 Hz. Every time the R-R interval decreases by 25%, the sampling rate is increased by 32 Hz up to 256 Hz. Equally, every time the R-R interval increases by 33%, the sampling rate is decreased by 32 Hz down to 32 Hz. In case that a maximum sampling rate of 1024 Hz is used, the range can be from 128 Hz to 1024 Hz by 128 Hz steps. According to certain embodiments, the system may include means for decreasing the sampling rate if the R-R interval increases more than 33% and increasing the sampling rate if the R-R interval decreases more than 25%, for instance. According to other certain embodiments, the sampling rate is increased or decreased if the difference in time between two consecutive heart beats is more than any predefined value in the range between 25 ms and 75 ms, for example more than 50 ms. According to certain embodiments, the sampling rate is increased if the heart rate is greater than a predefined value, for example greater than 180 bpm, 190 bpm, or 200 bpm.

Typically, the system includes means for storing the data measured with the increased heart rate. Data storage on the device may be e.g. accomplished by use of a removable memory such as a Micro SD card or any other suitable in-built memory. Direct data download may be e.g. accomplished by an on-board USB to a computer for transmittal to the physician or wirelessly by use of Bluetooth, Bluetooth Low Energy, WiFi or an 802.11 means to the Internet via a computer, a mobile device such as a smart phone or tablet for further transmission, processing and evaluation by a physician.

According to an embodiment, the first unit 3 of the monitoring system 1 has a short-range wireless transceiver which is preferably a transmitter operating on a wireless protocol, e.g. BLUETOOTH, part-15, or 802.11. "Part-15" refers to a conventional low-power, short-range wireless protocol, such as that used in cordless telephones. Other communication protocols include a part 15 low power short range radio, standard BLUETOOTH or BLUETOOTH Low Energy to conserve power or other low power short range communications means. The short-range wireless transmitter (e.g., a BLUETOOTH transmitter) receives information from the microprocessor and transmits this information in the form of a packet through an antenna. A second unit 4, for example a wristop-computer, an external laptop computer or a hand-held device features a similar antenna coupled to a matched wireless, short-range receiver that receives the packet. In certain embodiments, the hand-held device is a cellular telephone with a Bluetooth circuit integrated directly into a chipset used in the cellular telephone. In this case, the cellular telephone may include a software application that receives, processes, and displays the information. The secondary wireless component may also include a long-range wireless transmitter that transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof. Alternatively, the handheld device is a pager or PDA.

The system for heart rate monitoring 1 is powered by a power source. Preferably the power source is a battery. The power source may be a lithium ion rechargeable battery, for instance. The power source may have an accessible port for recharging. An alternative power source is e.g. an AA or AAA disposable or rechargeable battery. Battery consumption can be reduced by the system, because full wave forms of a pulse are only measured continuously in case of e.g. unexpected changes in the pulse-interval. Consequently, also memory space of the system 1 can be reduced, because only in case of continuous measurement of full wave forms of a pulse a substantial amount of data has to be stored.

The decision on changing the sampling rate may be also made by the first unit 3 according to certain embodiments. In other words, the decision on changing the sampling rate may be either made independently by the first unit or by the second unit according to the embodiments of the present invention. For example, the determination of the heart rate, the time difference between consecutive heart beats, or the time of each heart beat may be ambiguous, unclear or inaccurate for a specific reason and the first unit 3 may change the sampling rate independently in order to further obtain precise data. A signal from the second unit 4 may not be required in order to change the sampling rate.

In an embodiment, the decision making process may be, for example, based on a pNNx-value such as on the pNN50-value. The pNN50-value is a time domain measure of heart variability. The NN50 count is defined as the mean number of times per hour in which the change in consecutive sinus intervals exceeds 50 ms. For example, if the change in consecutive sinus intervals exceeds 50 ms, the latter sinus interval can be considered as "un-normal". The number of "un-normal" sinus intervals can be put in relation to the total number of sinus intervals within a certain time interval, e.g. within an hour or a minute. In case that the number of "un-normal" sinus intervals within a certain time interval exceeds a preset value, which preset value may be stored on a computer readable medium of the system for heart rate monitoring 1, the sampling rate may be changed. Accordingly, the sampling rate may be also changed if the change in consecutive sinus intervals is less than 10-20 ms, for instance. It is known that the change in consecutive sinus intervals e.g. of a 20 year old man is in the range between 30-130 ms and the change in consecutive sinus intervals of a 50 year old man is in the range between 20-40 ms. In other words, the "un-normal" sinus intervals may depend on the age of the user. Consequently, the system 1 in accordance with at least some embodiments of the invention may also take into account the age of the user for determining an "un-normal" sinus interval.

Alternatively, the decision making process may be, for example, based on a change of at least a part of the determined wave form of the heart beat signal. The frequency band related to the wave form of the heart beat signal is typically in the range between 17 Hz±10 Hz. In this range frequency responses of standard intervals between consecutive heart beats can be stored in a computer readable memory. The stored values may be fixed in the beginning, but may be subsequently personalized during use of the system 1. If the at least partially determined wave form of a heart beat signal (defined by the frequency response) differs too much from a stored heart beat signal wave form, the sampling rate may be increased. The decision may be based on the total power of the measured frequency band and if the change in the power is e.g. more than 15% the sampling rate is increased. The features (e.g. wave form) of standard heart rate should be stored for each sampling rate. The wave form definition (finger print) may be made every now and then even with a higher sampling rate in order to define PQRS form and further define if higher sampling rate (ECG) and storing is needed.

In an embodiment, at least a partial wave form or a full wave form of a heart beat signal is determined within a certain first time interval, for example every minute. In case that the at least partial wave form of the heart beat signal or the full wave form of the heart beat signal appears to be or is considered as "un-normal", the sampling rate as a response to the determined information is changed. Subsequent to changing the sampling rate, full wave forms of heart beats of the object are determined continuously or in second time intervals shorter than the first time interval. The determined information may be displayed and/or stored for further analysis.

According to a certain embodiment, other criteria for changing the sampling rate as a response to the determined information may be uploaded at a later stage and stored on a memory of the system. The system is configured to retrieve new criteria or instructions on how to use or interpret the measured data. The criteria or instructions may be individualized for use in connection with a particular user's heart beat measurements, for instance. In other words, new criteria or instruction based on which the sampling rate is changed can be transferred from a server infrastructure to the system.

Further, based on heart beat measurement data, which has already been measured and/or analyzed previously, the criteria or instructions for changing the sampling rate as a response to the determined information may be changed by an algorithm. Said algorithm may be considered as so called self-learning algorithm that can change different parameters based on already available data. The algorithm may be e.g. stored on the server infrastructure and may have access to a database comprising data which is linked to the ID of a single system in accordance with an embodiment of the present invention. Also the database may be e.g. stored on the server infrastructure. Users of the system may have access to individual data stored in the database via internet.

According to an embodiment, the system may comprise a memory configured to store first-type sensor data, at least one processing core configured to compile a message based at least partly on the first-type sensor data, to cause the message to be transmitted from the system, to cause receiving in the system a machine readable instruction, and using the machine readable instruction, based at least partly on sensor data. In other words, the sampling rate may be changed depending on the first-type sensor data. Examples of sensor data may be heart rate data, gyroscope data, magnetometer data, and location (GPS) data. Various embodiments of the system may comprise at least one feature from the following bulleted list:

- optionally, the estimated activity type and/or the nature of the activity may be derived from the first-type sensor data
- the machine readable instruction comprises at least one of the following: an executable program, an executable script and a set of at least two machine-readable characteristics, wherein each of the characteristics characterizes sensor data produced during a predefined activity type
- the at least one processing core is configured to derive the estimated activity type at least in part by comparing, using the machine readable instruction, the first-type sensor data, or a processed form of the first-type sensor data, to reference data
- the first-type sensor data comprises acceleration sensor data
- the memory is further configured to store second-type sensor data, and wherein the at least one processing core is configured to derive the estimated activity type, using the machine readable instruction, based at least in part on the second-type sensor data
- the second-type sensor data is of a different type than the first-type sensor data
- the second-type sensor data comprises at least one of: sound sensor data, microphone-derived data and vibration sensor data
- the at least one processing core is configured to derive the estimated activity type at least in part by comparing the second-type sensor data, or a processed form of the second-type sensor data, to reference data, the reference data comprising reference data of a first type and a second type
- the at least one processing core is configured to present the estimated activity type to a user for verification
- the at least one processing core is configured to cause the memory to store, in a sequence of estimated activity types, the estimated activity type and a second estimated activity type
- the at least one processing core is configured to cause the memory to delete the machine readable instruction responsive to a determination that an activity session has ended According to an embodiment, the system 1 can download criteria for changing the sampling rate based on a digital identification (ID). Different systems being wearable e.g. in the area of the hip, chest, or wrist may have different criteria for changing the sampling rate. The predetermined location of the system during use is known and criteria for changing the sampling rate may be downloaded based on the ID from a server infrastructure. The criteria for changing the sampling rate may be also updated by downloading new criteria replacing the previously existing criteria stored on the system. It may be also possible to choose criteria for changing the sampling rate from a list of various potential criteria via internet before use of the system. Thus, the system may be adapted for different applications and/or users.

In FIG. 2 a system is shown that can be used during a physical activity such as cycling. Of course, the system may also be used during a walking session, a jogging session, or any other sports session. Further, according to certain embodiments, the system may be used in medical applications.

Figure 3:
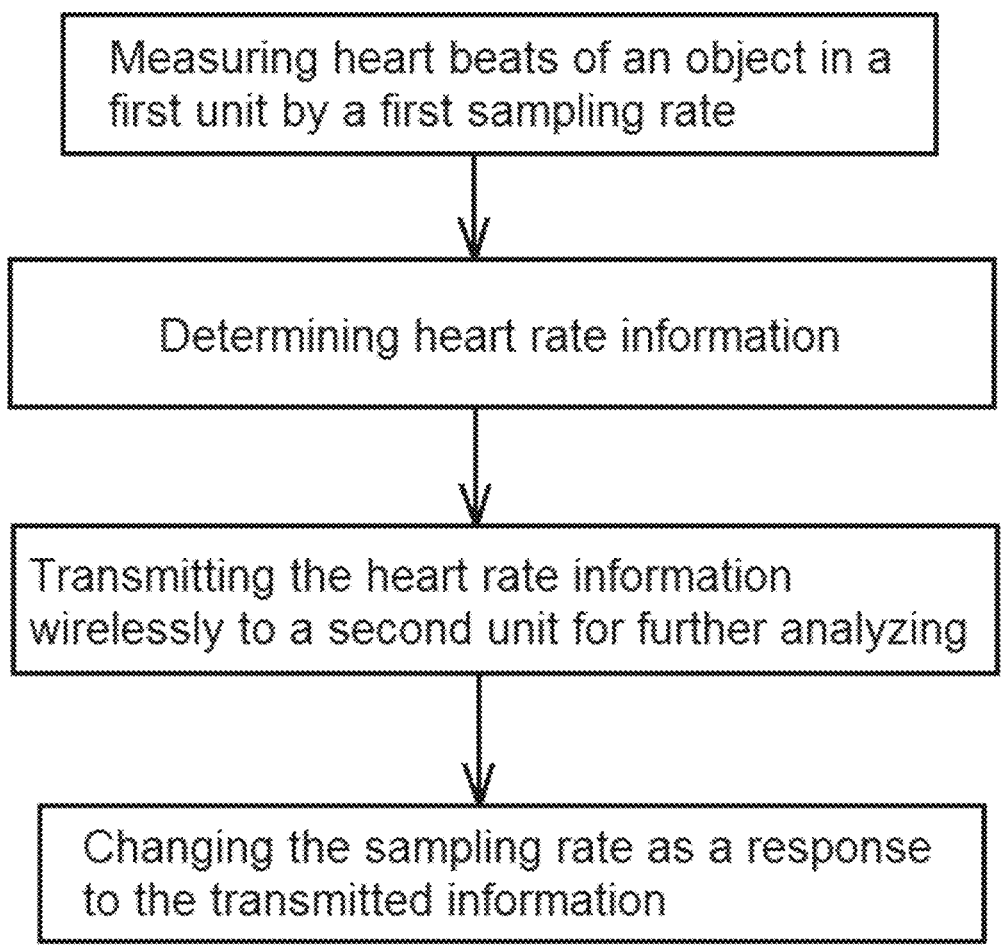
FIG. 3 illustrates a flow chart of a method for heart rate monitoring of an object in accordance with at least some embodiments of the present invention.

In FIG. 3 a flow chart of a method for heart rate monitoring of an object in accordance with at least some embodiments of the present invention is illustrated. In a first step the heart beats of an object are measured in a first unit by a first sampling rate. In other words, pulse data of a human is measured e.g. by means of a heart rate belt. Pulse-interval data can be determined from the measured heart beat information. The measured pulse-interval between consecutive heart beats does typically not vary or does only vary very limited within a certain tolerance range and is defined as $t_{norm}$, for instance.

Subsequently, the heart rate information, i.e. the pulse-interval data, is transmitted in a third step wirelessly to a second unit for further analyzing. The second unit may be, for example, a wristop computer or other computing device. The second unit may inter alia e.g. calculate the difference in consecutive pulse intervals.

In case that the difference in consecutive pulse intervals may be greater than a predefined tolerance value $\Delta t$, the sampling rate will be changed as a response to the transmitted information in a fourth step. The sampling rate is changed based on a beat-to-beat variability in R-R interval. In other words, if the difference in consecutive pulse intervals differs too much, the sampling rate is increased such that at least a partial wave form of one pulse can be formed. The first unit is configured to start to measure more pulse data than in the first step or first mode in such a case.

Figure 4:
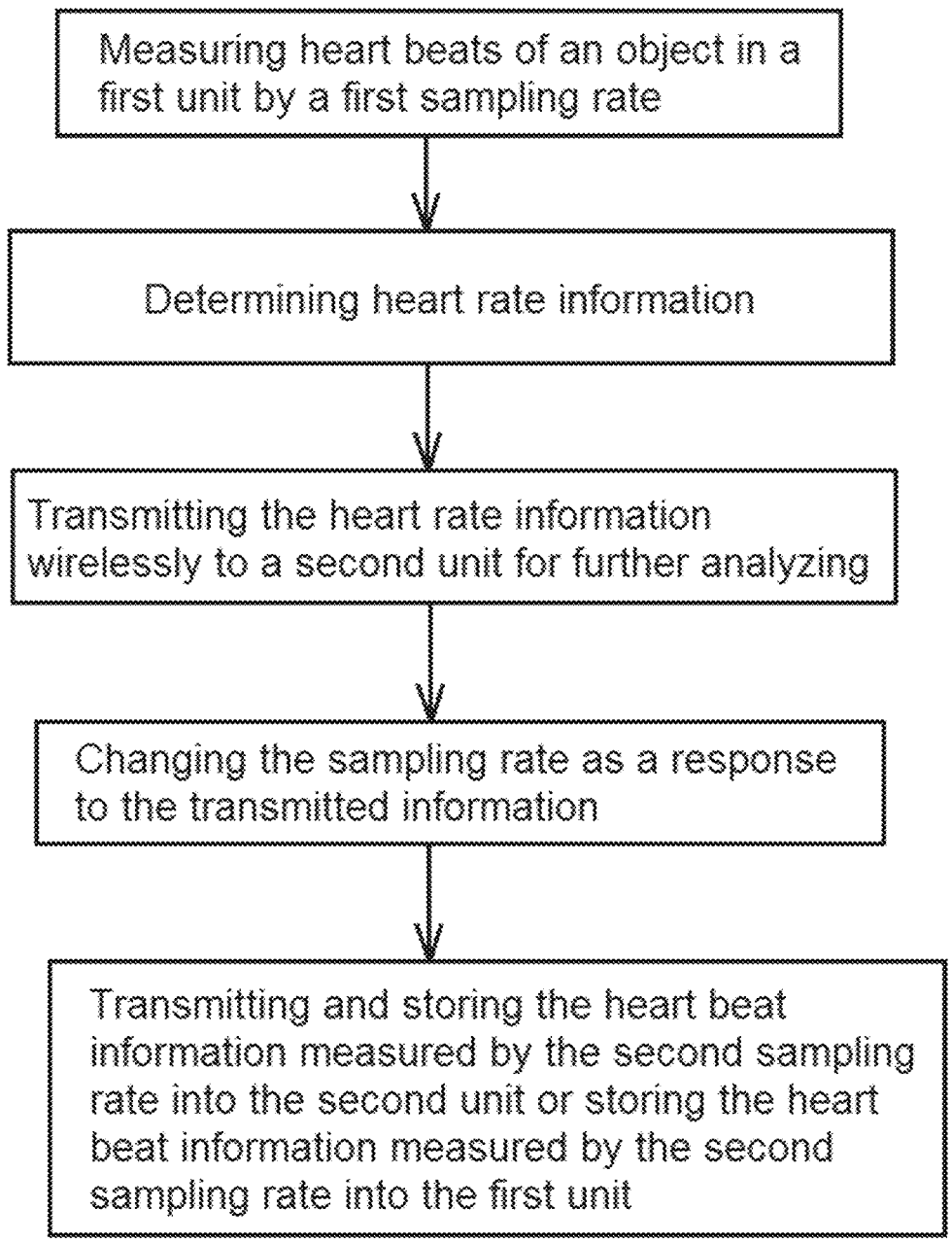
FIG. 4 illustrates a flow chart of a method for heart rate monitoring of an object in accordance with at least some embodiments of the present invention.

In FIG. 4 a flow chart of a method for heart rate monitoring of an object in accordance with at least some embodiments of the present invention is illustrated. The flow chart shows the same method steps as shown in FIG. 3 and additionally a fifth step is shown. In the fifth step the heart beat data measured by the second sampling rate is wirelessly transmitted to the second unit and stored into the memory of the second unit or directly stored into the memory of the first unit. The stored pulse data may be read out at a later stage or may be accessible in the memory for further analyzing by the second unit.

Figure 5:
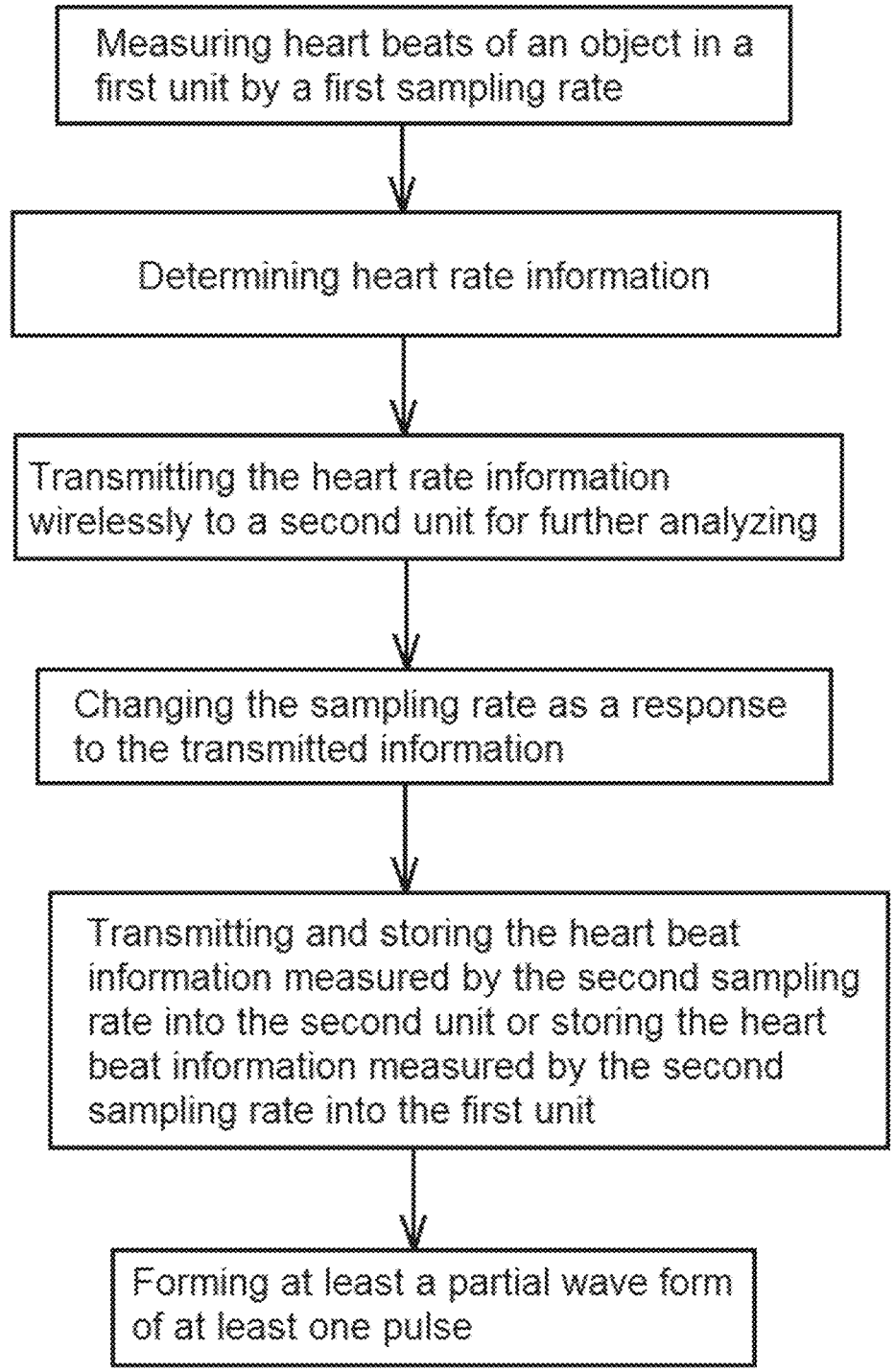
FIG. 5 illustrates a flow chart of a method for heart rate monitoring of an object in accordance with at least some embodiments of the present invention.

In FIG. 5 a flow chart of a method for heart rate monitoring of an object in accordance with at least some embodiments of the present invention is illustrated. The flow chart shows the same method steps as shown in FIG. 4 and additionally a sixth step is shown. In the sixth step at least a partial wave form of at least one pulse is formed. The at least partial wave form of the at least one pulse may be formed by the wristop computer 6 or by any other external computing device. The at least partial wave form of the at least one pulse is formed due to the beat-to-beat variability in R-R interval.

The at least partial wave form of the at least one pulse may be used by a doctor or other medical personal for diagnosis at a later stage. The system and method according to certain embodiments of the present invention can be utilized for obtaining pulse data. Detailed pulse data is only obtained in case of a beat-to-beat variability in R-R interval. Consequently, according to certain embodiments of the invention it is not necessary to monitor the wave forms of pulses continuously, but only in case of irregularities of the heart beats, which irregularities may be an indication of a physical problem of the heart. Thus, energy consumption and required memory availability can be reduced.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in wristop computers or similar systems for heart rate monitoring.

REFERENCE SIGNS LIST 1 system for heart rate monitoring
2 object
3 first unit
4 second unit
5 belt
6 wristop computer
$t_{norm}$ first pulse interval
$t_1$ second pulse interval

CITATION LIST

Patent Literature

U.S. D739,944 S
U.S. D739,943 S
U.S. D676,137 S
U.S. Pat. No. 9,167,975 B1
U.S. Pat. No. 9,179,849 B1
U.S. Pat. No. 9,314,174 B1
U.S. Pat. No. 9,144,385 B1
U.S. Pat. No. 8,974,396 B1
Non Patent Literature

The invention claimed is:

1. A system for heart rate monitoring of an object, wherein the system is configured to:
    measure heart beats of the object with a first unit in the form of a chest belt at a first sampling rate, wherein the chest belt comprises electrodes, and
    determine a heart rate, a time difference between consecutive heart beats, a time of each heart beat, or at least a part of a wave form of a heart beat signal,
wherein
    the system is configured to monitor an irregularity of the heart beats, and
    the first unit includes further a microprocessor configured to increase the first sampling rate to a second sampling rate as a response to the irregularity, wherein the microprocessor is configured to increase the first sampling rate so that at least a partial wave form of a pulse is formed.

2. The system for heart rate monitoring in accordance with claim 1, wherein the system is configured to wirelessly transmit the determined heart rate information, the determined time difference information, the determined time of each heart beat, or the at least partially determined wave form of a heart beat signal to a second unit for further analyzing.

3. The system for heart rate monitoring in accordance with claim 2, wherein the decision on changing the first sampling rate is made by the first unit or a second unit.

4. The system for heart rate monitoring in accordance with claim 1, wherein the microprocessor is configured to increase the first sampling rate when there is a decrease of more than 25% in a R-R interval.

5. The system for heart rate monitoring in accordance with claim 1, wherein the microprocessor is configured to decrease the second sampling rate when a R-R interval increases more than 33% and to increase the first sampling rate when the R-R interval decreases more than 25%.

6. The system for heart rate monitoring in accordance with claim 1, wherein it includes a memory for storing data measured with an increased heart rate.

7. The system for heart rate monitoring in accordance with claim 1, wherein the system is portable.

8. The system for heart rate monitoring in accordance with claim 1, wherein the system is configured to increase the first sampling rate based on a beat-to-beat variability in a R-R interval.

9. A method for monitoring a heart rate of an object, the method comprising:
    measuring heart beats of the object with a first unit in the form of a chest belt at a first sampling rate, wherein the chest belt comprises electrodes,
    determining a heart rate, a time difference between consecutive heart beats, a time of each heart beat, or at least a part of a wave form of a heart beat signal, and
    monitoring an irregularity of the heart beats, and
    increasing the first sampling rate to a second sampling rate as a response to the irregularity by the first unit increasing the first sampling rate so that at least a partial wave form of one pulse is formed.

10. The method for monitoring a heart rate of an object according to claim 9, wherein the determined heart rate information, the determined time difference information, the determined time of each heart beat, or the at least partially determined wave form of a heart beat signal is wirelessly transmitted to a second unit for further analyzing.

11. The method for monitoring a heart rate of an object according to claim 9, wherein a decision on changing the first sampling rate is made by the first unit or the second unit.

12. The method for monitoring a heart rate of an object according to claim 9, wherein the first sampling rate is increased when there is a decrease of more than 25% in a R-R interval.

13. The method for monitoring a heart rate of an object according to claim 9, wherein the second sampling rate is decreased when a R-R interval increases more than 33% and the first sampling rate is increased when the R-R interval decreases more than 25%.

14. The method for monitoring a heart rate of an object according to claim 9, wherein data measured with the increased second sampling rate is stored.

15. The method for monitoring a heart rate of an object according to claim 9, wherein the first sampling rate is increased based on a beat-to-beat variability in a R-R interval.

16. The method for monitoring a heart rate of an object according to claim 9, wherein at least a part of a wave form of a heart beat signal is determined at the first sampling rate in first time intervals and subsequently at least a part of a wave form of a heart beat signal is determined at the second sampling rate continuously or in second time intervals shorter than the first time intervals.

17. A non-transitory computer readable medium having stored thereon a set of computer readable instructions that, when executed by at least one processor, cause an apparatus to at least:
    measure heart beats of an object with a first unit in the form of a chest belt at a first sampling rate, wherein the chest belt comprises electrodes,
    determine a heart rate, a time difference between consecutive heart beats, a time of each heart beat, or at least a part of a wave form of a heart beat signal, and
    monitor an irregularity of the heart beats, and
    increase the sampling rate as a response to the irregularity.

18. The system for heart rate monitoring in accordance with claim 1, wherein the system is configured to increase the sampling rate as a response to the irregularity in the form of atrial fibrillation.

19. The method for monitoring a heart rate of an object according to claim 9, wherein increasing the sampling rate takes place as a response to the irregularity in the form of atrial fibrillation.

20. A system for heart rate monitoring of an object, wherein the system is configured to:
   measure heart beats of the object with a first unit in the form of a chest belt at a first sampling rate, wherein the chest belt comprises electrodes, and
   determine a heart rate, a time difference between consecutive heart beats, a time of each heart beat, or at least a part of a wave form of a heart beat signal,
wherein
   the system is configured to monitor an irregularity of the heart beats, and
   the first unit includes further a microprocessor configured to increase the first sampling rate as a response to the irregularity,
   wherein the microprocessor is configured to increase the first sampling rate to a second sampling rate when there is a decrease of more than 25% in a R-R interval.

21. The system for heart rate monitoring in accordance with claim 20, wherein the microprocessor is configured to decrease the second sampling rate when the R-R interval increases more than 33%.

22. A method for monitoring a heart rate of an object, the method comprising:
   measuring heart beats of the object with a first unit in the form of a chest belt at a first sampling rate, wherein the chest belt comprises electrodes,
   determining a heart rate, a time difference between consecutive heart beats, a time of each heart beat, or at least a part of a wave form of a heart beat signal, and
   monitoring an irregularity of the heart beats, and
   increasing the sampling rate as a response to the irregularity by the first unit, wherein
   the first sampling rate is increased to a second sampling rate when there is a decrease of more than 25% in a R-R interval.

23. The method for monitoring a heart rate of an object according to claim 22, wherein the second sampling rate is decreased when the R-R interval increases more than 33%.

* * * * *